(12) United States Patent
Xu et al.

(10) Patent No.: US 7,131,461 B2
(45) Date of Patent: Nov. 7, 2006

(54) STREAM SWITCHING SYSTEM (75) Inventors: Yang Xu, Houston, TX (US); Teresa Lechner-Fish, Houston, TX (US)

(73) Assignee: Daniel Industries, Inc., Houston, TX (US)

( * ) Notice: Subject to any disclaimer, the term of this patent is extended or adjusted under 35 U.S.C. 154(b) by 429 days.

(21) Appl. No.: 09/538,455

(22) Filed: Mar. 30, 2000

(65) Prior Publication Data

US 2002/0007858 A1 Jan. 24, 2002

Related U.S. Application Data (60) Provisional application No. 60/141,357, filed on Jun. 28, 1999.

(51) Int. Cl.
*F15C 1/04* (2006.01)
(52) U.S. Cl. .............. 137/828; 137/341; 137/549; 137/883; 137/884; 251/129.15
(58) Field of Classification Search ............. 137/828, 137/883, 884, 549, 550, 341; 251/129.15
See application file for complete search history.

(56) References Cited

U.S. PATENT DOCUMENTS

| | | | | |
|---|---|---|---|---|
| 4,612,959 A | * | 9/1986 | Costello | ............ 137/828 |
| 4,846,218 A | * | 7/1989 | Upchurch | ............ 137/544 |
| 4,994,180 A | * | 2/1991 | Sims et al. | ............ 210/198.2 |
| 5,201,219 A | | 4/1993 | Bandurski et al. | ............ 73/153 |
| 5,544,276 A | * | 8/1996 | Loux et al. | |
| 5,653,259 A | | 8/1997 | Ramstad | ............ 137/606 |
| 5,686,657 A | * | 11/1997 | Craig et al. | ............ 73/23.42 |
| 5,964,239 A | * | 10/1999 | Loux et al. | ............ 137/15 |
| 6,102,068 A | * | 8/2000 | Higdon et al. | ............ 137/341 |

FOREIGN PATENT DOCUMENTS

| | | |
|---|---|---|
| EP | 0 583 166 A2 | 2/1994 |
| FR | 2 664 671 | 1/1992 |
| WO | WO 97/19283 | 5/1997 |

* cited by examiner

*Primary Examiner*—A. Michael Chambers
(74) *Attorney, Agent, or Firm*—Conley Rose PC (57) ABSTRACT

An improved double block and double bleed stream switching system (modifiable to, for example, a double block, single bleed stream switching system) includes a common stream path for a multitude of gas streams from, for example, a process pipeline. The improved stream switching system includes a heating mechanism and insulation oven to help temperature stabilization, along with a structure to separate temperature sensitive solenoids from the heated area. Pre-heat coils are located between the sample switching system and the sample shut off system to warm the gas sample and to act as a flow restrictor. A first embodiment is suited for the Division 1 environment and a second embodiment is suited for Division 2 uses. The improved stream switching system may also feature membrane or cartridge filters located upstream of the sample wetted portion of the stream switching system.

17 Claims, 12 Drawing Sheets

STREAM SWITCHING SYSTEM

CROSS-REFERENCE TO RELATED APPLICATIONS

This application claims priority to provisional application No. 60/141,357 filed Jun. 28, 1999.

STATEMENT REGARDING FEDERALLY SPONSORED RESEARCH OR DEVELOPMENT

Not Applicable.

BACKGROUND OF THE INVENTION

It is often very important to know what fluids are flowing through a conduit such as a pipeline. For example, a buyer and seller may agree upon a price for the fluid flowing through a process pipeline based upon the content of the fluid stream. Thus, the fluid content must be measured. Where multiple pipelines are positioned near one another, it may be economical to use a single meter or measurement device to monitor all of the fluid flows. The device used to extract and deliver the fluid to the measurement device is traditionally referred to as a sampling system.

Figure 1:
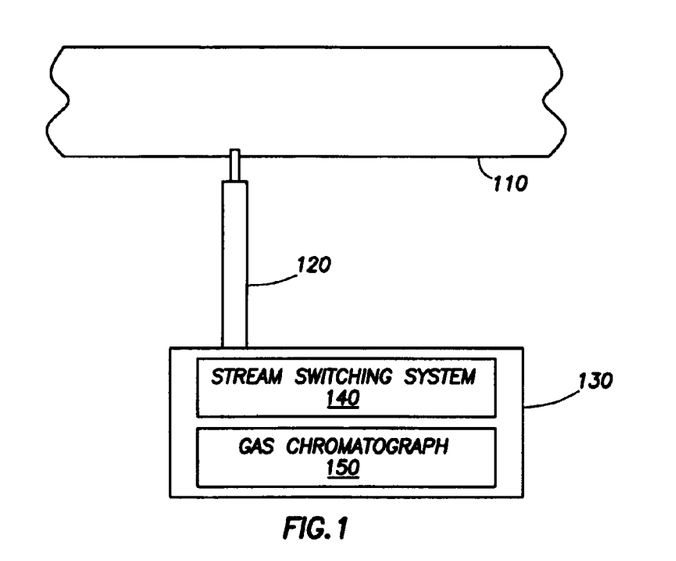
FIG. 1 is a prior art sample handling system.

FIG. 1 includes a stream sampling system ("sampling system") 100. Although only a single pipeline is shown, it is to be understood that multiple pipelines may be present. Sampling system 100 includes a sample point attached to pipeline 110, an analyzer 130, and tubing 120 from the sample point to the analyzer 130. Analyzer 130 may include a stream switching system 140 and gas chromatograph 150. In operation, fluid flow through a process pipeline 110. The sample point (preferably a probe fluid) obtains a sample of fluid and delivers it to analyzer 130 via tubing 120. Analyzer 130 measures the content of the fluid sample and either returns the sample to the pipeline or vents the sample to the ambient environment.

One problem with such a layout is the large distance from the analyzer 130 to the pipeline 110, which creates a large "dead volume" of fluid. Increased dead volume results in undue mixing of consecutive fluid samples. This mixing of fluid samples results in "carry-over" between samples for gas chromatograph analysis. Carry-over is undesirable because accurate analysis requires that the analysis is representative of the fluid in the process pipeline. Since the volume of transport tubing and stream sampling components must be flushed a minimum of ten times to insure a representative sample, the "dead volume" results in significant lag time between sample analysis. Therefore, upon a sampling of fluid from the pipeline 110, the "dead volume" of fluid must be vented or otherwise disposed of before the new sample can be measured at the analyzer 130. Further, although the magnitude of the "dead volume" could be reduced by placing the analyzer 130 closer to the sample point 110, regulations and safety concerns mandate a minimum 50 feet distance between them. If placed closer than 50 feet from the pipeline 110, the analyzer 130 must be contained in an expensive explosion-proof housing.

Figure 2:
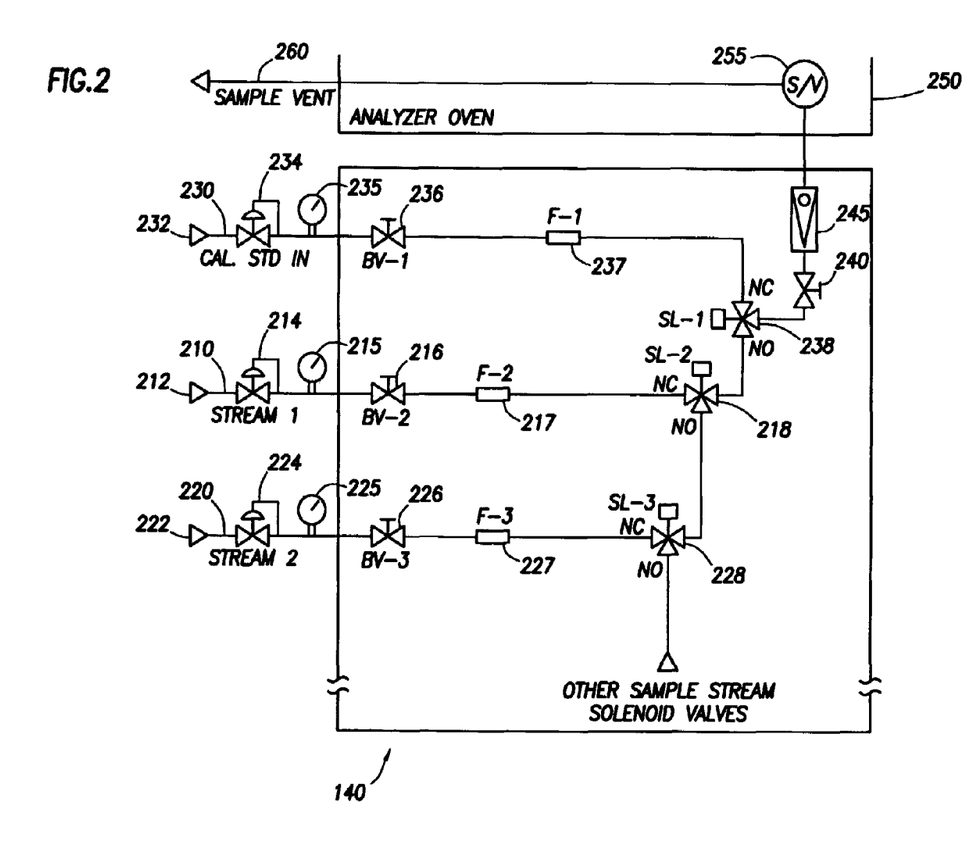
FIG. 2 is a prior art stream switching system.

FIG. 2 includes a stream switching system 140 attached to an analyzer oven 250 that is part of gas chromatograph 150. Three pipes or tubes 210, 220, 230 attach to switching system 140, and correspond to first, second and third flow paths. The first pipe or tube 210 connects to a first sample point 212 and carries a first gas stream of unknown composition from, for example, a process pipeline. Included along "stream 1" are pressure regulator 214 and pressure gage 215, shut-off valve 216, particulate filter 217, and a first stream switching valve 218. Second pipe or tube 220 connects to a second sample point 222 and carries second gas stream of unknown composition. Included along "stream 2" are pressure regulator 224 and pressure gage 225, shut-off valve 226, particulate filter 227, and a second stream switching valve 228. The third pipe or tube 230 connects to a third sample point 232 and a calibration sample of known composition. Included along the third path are pressure regulator 234 and pressure gage 235, shut-off valve 236, particulate filter 237, and a third switching valve 238. Third switching valve 238 connects not only to filter 237, through one port, but also to first and second switching valves 218, 228 through another. Yet another port of third switching valve 238 attaches to regulator 240 and flow meter 245. Flow meter 245 attaches through a relatively long tube to sample shut-off valve 255 housed in analyzer oven 250. Sample valve 255 connects to a sample valve in the oven, and then connects to the vent 260. As can be appreciated, although only two streams of unknown fluids are shown, additional streams could be added by the use of a greater number of flow paths.

During operation, a gas chromatograph housed in analyzer oven 250 is calibrated using the calibration sample from sample point 232. The pressure and flow rate of this stream are maintained by pressure regulator 234, regulator 240 and flow meter 245. Because the composition of the calibration sample is known, it may be used to calibrate the gas chromatograph. The calibration sample flows through third switching valve 238, through the gas chromatograph 150 and out sample vent 260. If a measurement of the fluid at sample point 222 is desired, the gas along the second pipe is allowed to flow by actuation of second stream switching valve 228, through first stream switching valve 218, and through third stream switching valve 238. The third switching valve 238 is the only valve in the stream switching system that on its own can prevent or block the flow of fluid from all the sample points. Thus, this configuration is referred to as a "single block" stream switching system. One drawback of this design is that the fluid from sample point 222 flows through all of the first, second, and third switching valves prior to arrival at the gas chromatograph, and malfunction of only a single one of these switching valves prevents the measurement of a sample of fluid from stream 2.

If, after the above-described measurement of stream 2, it is desired to measure the fluid from stream 1, the system must be purged of the previous fluid sample. Purging of the old fluid stream from the system prevents contamination between the streams. Thus, the stream switching system of FIG. 2 would switch from stream 2 to stream 1. At that time, adequate accuracy by the gas chromatograph has likely been assured if all the other necessary criteria have been met. Many refer to a configuration having a single sample vent as a "single bleed" stream switching system.

Thus, a "dead volume" of fluid in a stream switching system is a significant problem. Another problem encountered in a stream switching system is the reliability and maintenance of the system. Because an operator may visit a particular stream switching system only infrequently, the system should be accurate, reliable, as immune to breakdown as possible, and simple to repair when problems do occur. This highly sought after combination of features is not available with current stream switching systems.

Another drawback in many prior systems is their difficulty in analyzing a complex fluids because of limitations in the associated gas chromatographs. It would be desirable if a stream switching system could be developed that could quickly transfer fluid sample to the analyzer. This drawback also reduces the usefulness of a stream sampling system.

A stream sampling system is needed that is faster, more reliable, more flexible, and more accurate than previous stream sampling systems. Ideally, such a stream sampling system could reduce the adverse effects of "dead volume." This ideal stream sampling system would also be less prone to breakdown than previous models, while providing much faster and more accurate measurements.

SUMMARY OF THE INVENTION

The invention features a stream switching system including a housing having a common stream path with multiple input ports and at least one output port, tubing connected to the output port, the tubing including a heating coil to heat and control the flow rate of a fluid sample traveling through the heating coil. An insulated housing encapsulating the stream switching housing may be included to stabilize the temperature of the stream switching housing. A silicone rubber heater may also be attached to the stream handling housing. Numerous solenoids or other fluid flow activation switches also connect to the stream switching housing and preferably are positioned outside of the insulated housing.

Another inventive feature of the stream switching system is the use of fluid flow switches (such as solenoids attached to a pressurized line) that prevent the flow of gas while an outside impulse is being applied. This prevents stream switching system leakage during, for example, power failure. The invention also includes a stream switching system having a sample point, a stream switching portion, tubing connecting the two, and one or more membrane or cartridge filters located proximate (preferably within 10 feet and even more preferably within 3 feet) the sample point.

Thus, the invention comprises a combination of features and advantages which enable it to overcome various problems of prior devices. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made to the accompanying drawings, wherein:

FIG. 16 is a prior art sample handling system.

DETAILED DESCRIPTION OF THE PREFERRED EMBODIMENT

Figure 3:
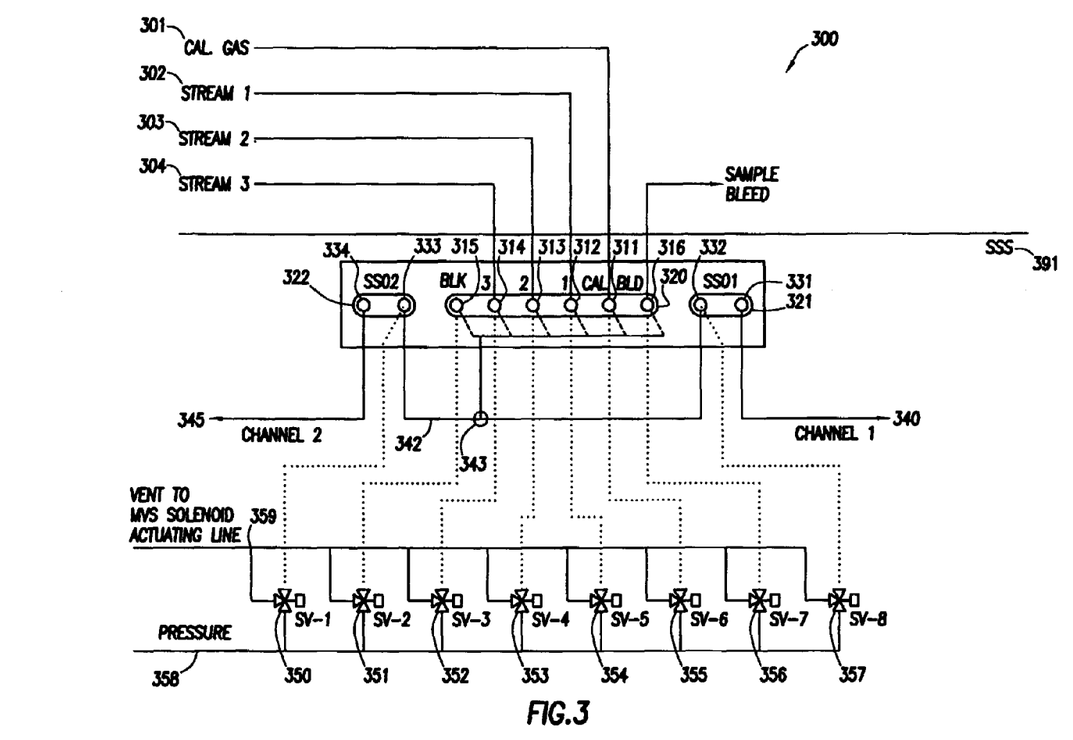
FIG. 3 is a schematic of a stream switching system according to an embodiment of the present invention.

FIG. 3 shows a "double block and double bleed" of one preferred embodiment of a stream switching system according to the invention. The stream switching system 300 includes four streams upstream of a stream handling portion 391. Four streams include a calibration sample 301, 101 stream 1 302 corresponding to a first fluid sample, stream 2 303 corresponding to a second fluid sample, and stream 3 304 corresponding to a third fluid sample. It is to be understood that more or fewer ports can be included and that one or more separate stream switch systems could be included.

Streams 301–304 supply various fluid samples to the sample wetted portion, and connect respectively to actuatable calibration port 311 and actuatable stream ports 312–314. Actuatable ports 315–316 and 332–333, as well as ports 331 and 334, are also part of the sample wetted portion 391. Each actuatable port may be actuated into either an open or closed state as controlled by eight connected solenoids 350–357 (also labeled SV1–SV8) which correspond respectively to ports 311–316, 332–333. When a port is in an open state, fluid may pass freely through the port. When a port is in a closed state, fluid is prevented from flowing through that port. Also shown in FIG. 3 are solenoid pressure line 358 and solenoid vent line 359, as well as gas path 342 extending from port 315 to ports 333 and 332.

As explained further below, each actuatable stream port 312–314, as well as actuatable calibration port 311, is positioned in an area 320 that creates a common sample path. Also positioned in the common sample path 320 are an actuatable "blocking" port 315 and an actuatable "bleed" port 316. In addition, area 321 creates a first sample shut off that contains two "blocking" ports 332 and port 331. Area 322 creates a second sample shut off that contains two "blocking" ports 333 and port 334. As shown, ports 332 and 333 are actuatable, while ports 331 and 334 are not. It is to be understood, however, that all of these ports could be actuatable, or that ports 332 and 333 could be actuatable while ports 331 and 334 are not.

Two channels, channel 1 340 and channel 2 345, are output tubing that direct fluid sample away from the stream switching system. As used with reference to the invention, the term tubing is used in a general manner and includes other fluid transportation mediums such as piping. The channels connect to, for example, downstream gas chromatographs including valve, heating, and measurement devices. Each channel thus may be separately analyzed by a gas chromatograph. Each channel can also be used as a flow path to "bleed" the system when switching from sample point to sample point.

As can also be appreciated, first and second sample shut offs correspond to first and second channels 340, 345. Consequently each channel is associated with two solenoids 350 and 357, either one of which can be actuated to prevent the flow of any fluid through the channel. It can be appreciated that the use of a solenoid to prevent the flow of fluid is not absolutely necessary, and any suitable mechanical or electrical gas flow actuation switch may be used. In the illustrated embodiment, the flow of fluid through channel 1 may be prevented by closing either actuatable blocking port 315 or actuatable port 332 in the first sample shut off. Similarly, the flow of fluid through channel 2 may be prevented by closing either actuatable blocking port 315 or the actuatable port 333 in the second sample shut off. Thus, because the flow of fluid may be prevented through a channel at either of two locations, this is a "double block" design. In addition, the system may be bled through sample bleed port 316. Thus, because the system may be bled either through a channel or through the sample bleed port 316 the embodiment is a "double bleed" design.

Figure 4:
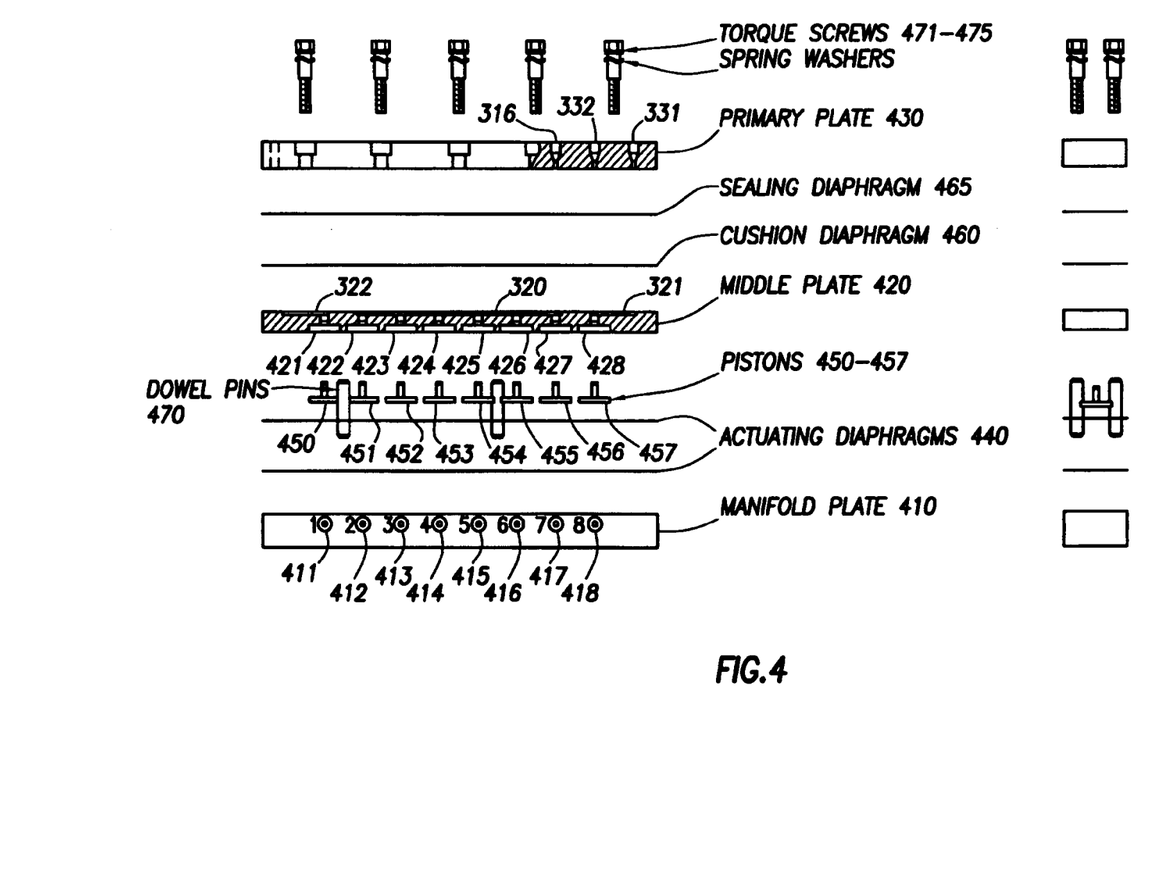
FIG. 4 is an exploded side view of the embodiment of FIG. 3.

Referring now to FIG. 4, a side exploded view of the stream switching portion 391 is shown. In this embodiment, the stream switching portion constitutes upper, middle, and lower plates aligned and connected together by dowel pins 470 and torque screws 471–475. The lower plate, referred to as a manifold plate 410, includes eight actuation ports 411–418 connected by tubing to solenoids 350–357 (not explicitly shown in FIG. 4). The middle plate, also called a piston plate 420, includes eight locations 421–428 designed to receive respective pistons 450–457. Middle plate 420 also includes shallow channels, chambers, or grooves that form areas 320–322, as described with reference to FIG. 3. The upper plate, referred to as the primary plate 430, includes screw holes corresponding to the torque screws, as well as three exemplary fluid ports 316, 332, and 331. Eight pistons 450–457 (corresponding to ports 311–316, 332–333) as well as a pair of actuating diaphragms 440 lie between manifold plate 410 and middle plate 420. Sealing diaphragm 465 and cushion diaphragm 460 lie between the primary plate 430 and middle plate 420. These diaphragms ensure a leak-free fit between each pair of plates and between a piston and its corresponding port. The actuating diaphragms may be made from Kapton of about 3 mm thickness. Similarly, the sealing diaphragms may be made from Teflon coated Kapton. However, as would be appreciated by those of ordinary skill, the invention is not limited solely to these sealing diaphragms.

Figure 5:
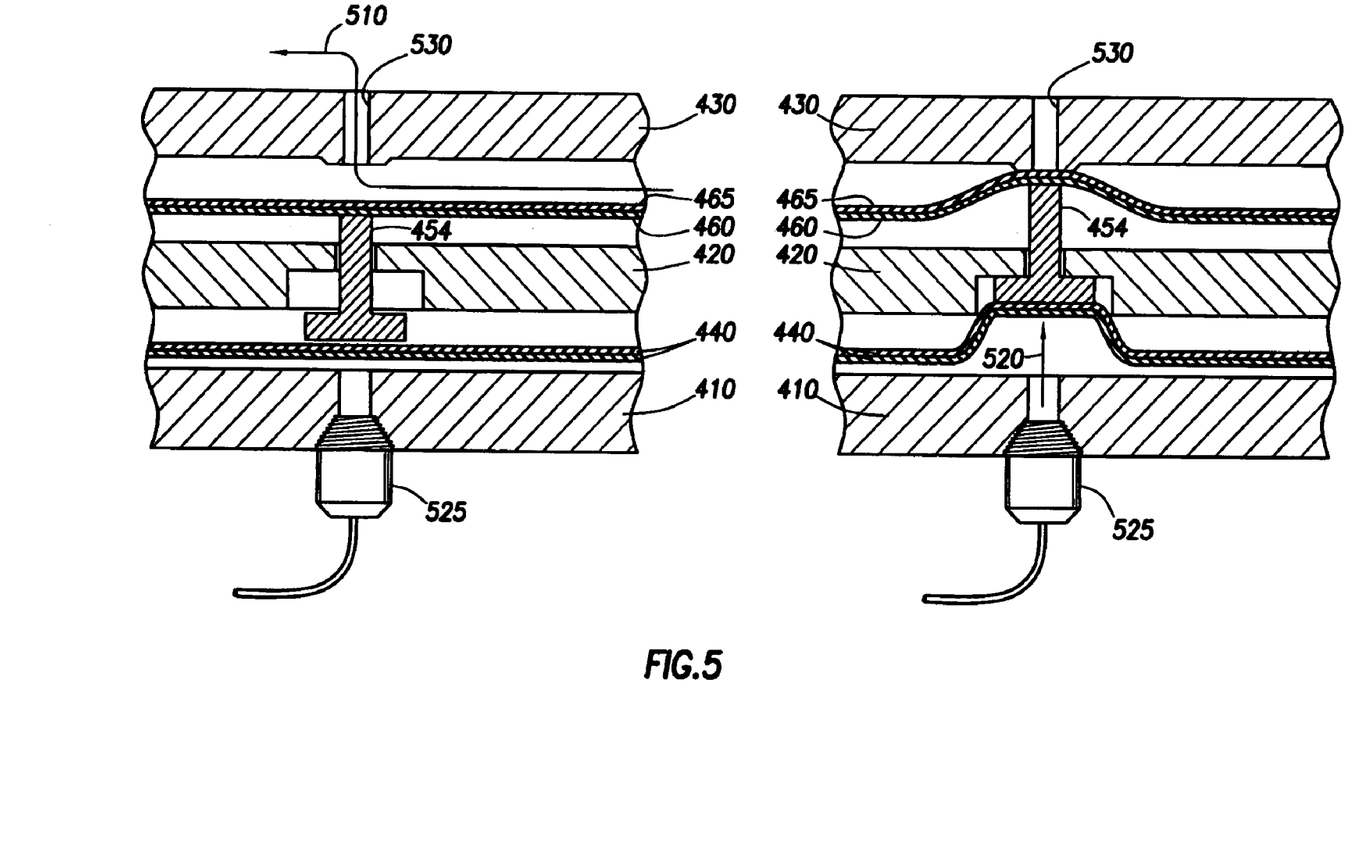
FIG. 5 is a magnified view of FIG. 4.

FIG. 5 includes a close-up view of piston 454, manifold plate 410 with attached solenoid or other appropriate fluid flow activation switch, middle plate 420, primary plate 430 including passage 530 (corresponding to one of the ports illustrated in FIGS. 3 and 4), and diaphragms 440, 460, and 465. The left portion of FIG. 5 includes a fluid stream 510 such as a calibration gas or fluid sample. The right portion of FIG. 5 includes actuation gas 520. When a port is open (as shown on the left side of FIG. 5), a fluid stream 510 between primary plate 430 and diaphragm 465 exits through passage 530. Conversely, when a port is closed (as shown on the right), there is no flow of a fluid stream 510. Instead, an actuation gas 520 is applied by the solenoid 525 against the piston head of piston 454. The piston 454 is forced upward, with its narrow end abutting the lower end of passage 530 formed in primary plate 430. Because the relatively large surface area of its head is presented to the actuating fluid 520, the piston 454 inherently multiplies the force available such that a gas tight seal is formed against the passage 530. As can be appreciated, a piston is not the only possible actuation member, with suitable devices including solenoids, flapper valves, direct diaphragm valves, and others.

Referring to FIG. 3, a sample from stream 1 302 will be used to illustrate the operation of the device. The pressure in each stream from a pipeline is normally reduced to about 15–25 psi. Consequently, a sample from, for example, a process pipeline travels to channel 320 via port 312 when port 312 is open. Port 312 being open corresponds to piston 454 being in a lower position. As can be understood from FIG. 4 and as is shown in FIG. 5, the piston 454 is forced to this lower position from the fluid pressure applied through stream 1 302 and a lack of actuation pressure applied by solenoid 354. Gravity may also assist in the piston falling to a lower position. To avoid cross-contamination, when port 312 is open, ports 311, 313, and 314 are, therefore, closed in normal operation. This closure of ports 311, 313, and 314 corresponds to pistons 455, 453 and 452 being in an elevated position by activation fluid pressure applied through solenoids 355, 353 and 352. As can consequently be appreciated, the assembly shown in FIG. 4 need not be vertical, but instead can operate from a variety of angles, and the use of terms such as "lower" and "upper" is merely for explanatory purposes.

The fluid sample travels through port 312 and along common stream channel 320 to blocking port 315, which is also open by operation of the associated solenoid. The sample then travels through blocking port 315 and along gas path 342 that includes a "T" at point 343. This "T" intersection at point 343 splits the sample into two portions. A first portion travels to sample shut off channel 321 via actuatable port 332. When port 332 is open, the sample travels along the sample shut off channel to port 331, which then allows this first portion of the sample to flow out channel 1 340 to a first gas chromatograph (not shown). A second portion of the sample travels to sample shut off channel 322 via an open actuatable port 333. Port 334 allows this second portion of the sample to flow out channel 2 345 to a second gas chromatograph (not shown). As would be appreciated by one of ordinary skill in the art, gas path 342 may be external tubing or may be milled into one or more plates, such as lines permanently drilled into primary plate 430.

The double block and double bleed design of this embodiment has particular advantages. For example, when switching from stream 1 to stream 2, the system must be bled. First, the sample shut offs are closed to block the flow stream by the closure of sample shut off ports 332 and 333 by actuation of solenoids 350 and 357. Stream port 312 is also closed to block the flow of pressurized gas from stream 1. A short time thereafter, sample bleed port 316 in the common stream path is opened while port 315 is still open, allowing the pressurized gas in common stream path 320 to equalize to atmospheric pressure. Simultaneously, inside the associated gas chromatograph 150, the carrier gas associated with the well-known operation of the chromatographic valve sampling injects an aliquot of sample fluid for analysis by the gas chromatograph. When this occurs, the remaining fluid in the system downstream of the sample shut offs is allowed to equalize to atmospheric pressure. At that time, the sample shut offs can be opened, the sample bleed port 316 closed, and the system purged with the new stream from stream 2. Because the pressure of the stream switching system has already been lowered to atmospheric pressure, and because stream 2 is under pressure, the sample from stream 2 will quickly flow through the stream switching system. This results in a faster purging with lower volumes of the new sample being necessary.

As an additional benefit to this embodiment, the use of two channels allow near-parallel analysis by separate gas chromatographs or detectors within the same gas chromatograph, which can speed the sample analysis of a complex sample having numerous components. For example, an open first sample shut off and closed second sample shut off allows sample to flow through channel 1 for a period of five seconds. An open second sample shut off and closed first shut off could them allow sample to flow through channel 2 for the next five seconds. This results in near-simultaneous analysis by the gas chromatographs or detectors.

Moreover, this design is particularly desirable because the advantages recited above are achieved without the expense otherwise necessary (such as for extra valves, etc) to attain a double block and double bleed configuration. Further, the above design can be easily modified for particular situations. For example, additional ports can be freed for use as stream ports if only single blocking or only a single channel is desired. The design can also be modified to be a single bleed design, if desired. The design may also be modified to add or subtract parts as necessary.

Improvements to this design are also possible. For example, it is known to modify the design of FIG. 2 to include membrane filters that by-pass liquid condensate as shown in FIG. 16. Membrane filters prevent condensate in the pipeline from flowing into the stream switching system, which can contaminate the gas chromatograph.

FIG. 16 includes a stream switching system attached to an analyzer oven 1650 that is part of gas chromatograph 150. Three input pipes or tubes 1610, 1620, 1630 attach to switching system 140, and correspond to first, second and third flow paths. The first pipe or tube 1610 connects to a first sample point 1612 and carries a first fluid stream of unknown composition from, for example, a process pipeline. Included along "stream 1" are pressure regulator 1614 and pressure gage 1615, shut-off valve 1616, particulate filter 1617, and a first stream switching valve 1618. Interposed between particulate filter 1617 and first stream switching valve 1618 is membrane filter 1670. Connected to membrane filter 1670 are flow meter 1671, valve 1672, and bypass line 1611 for alternate expulsion of sample from "stream 1." Second pipe or tube 1620 connects to a second sample point 1622 and carries second fluid stream of unknown composition. Included along "stream 2" are pressure regulator 1624 and pressure gage 1625, shut-off valve 1626, particulate filter 1627, and a second stream switching valve 1628. Interposed between particulate filter 1627 and first stream switching valve 1628 is membrane filter 1680. Connected to membrane filter 1680 are flow meter 1681, valve 1682, and bypass line 1621 for alternate expulsion of sample from "stream 2." The third pipe or tube 1630 connects to a third sample point 1632 and a calibration gas stream of known composition. Included along the third path are pressure regulator 1634 and pressure gage 1635, shut-off valve 1636, particulate filter 1637, and a third switching valve 1638. Third switching valve 1638 connects not only to filter 1637, through one port, but also to first and second switching valves 1618, 1628 through another. Yet another port of third switching valve 1638 attaches to regulator 1640 and flow meter 1645. Flow meter 1645 attaches through a relatively long tube to sample shut-off valve 1655 housed in analyzer oven 1650. Also connected to sample shut-off valve 1655 is sample vent 1660. As can be appreciated, although only two streams of unknown gas are shown, additional streams could be added by the use of a greater number of flow paths. As can be appreciated, the membrane filters of FIG. 16 are located close to the stream switching valves. This location for the membrane filters eliminates liquid condensate from sample immediately upstream from chromatograph sample valve, if desired.

Figure 6:
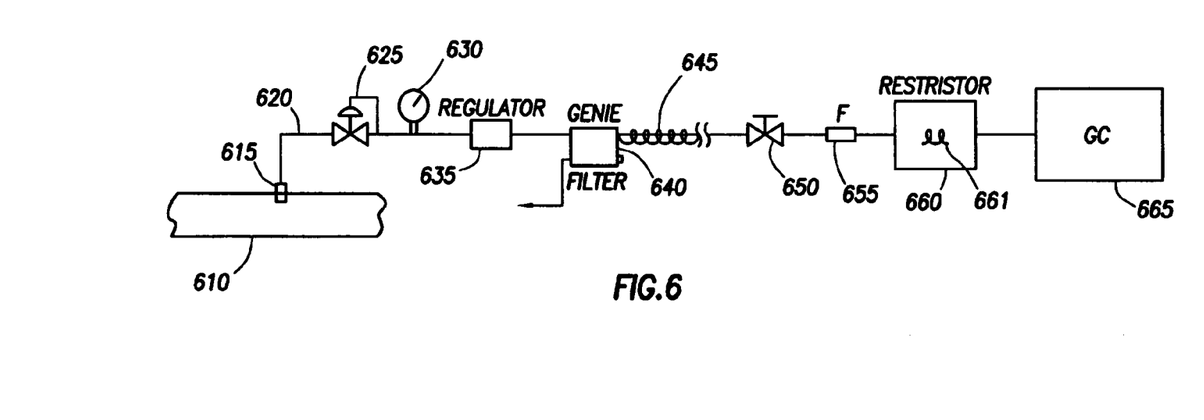
FIG. 6 is an improved sample handling system according to an embodiment of the invention.

The inventive arrangement of FIG. 6 includes a sample point (preferably a probe) 615 that is located at, for example, process pipeline 610. Attached to sample probe 615 is a sample flow path that includes tubing or piping 620, a pressure regulator 625, pressure gage 630, regulator 635, one or more membrane filters 640, heat tracing 645, valve 650, particulate filter 655, sample switching system 660 including a flow restristor and pre-heat coil 661, and gas chromatograph 665.

As can be appreciated, in this embodiment the membrane filter(s) 640 are located not in the sample switching system 660, but instead are located near the sample point. These filters are preferably within ten feet, and even more preferably, within three feet of the sample point. Placement of the membrane filters 640 as close to the sample point 610 as feasible results in a number of advantages. For example, because every device in the stream has an associated pressure drop, the closer the filter is to the sample point, the lower the pressure needed in the overall system to force the sample through the filter. Therefore, the embodiment of FIG. 6 has sufficient pressure to force the sample gas through the membrane filter. In addition, membrane filters require occasional replacement. Placement of the membrane filter close to the sample point, and the accompanying lower pressure necessary to operate the system, results in a longer life filter. Further, if and when the filter's operating life does expire, the location of the filter outside the stream switching system simplifies replacement and maintenance. This location for the membrane filter also simplifies the heating of the sample on the sample handling system, if desired. This design change could also be applied to cartridge filters with a similar result.

Figure 7:
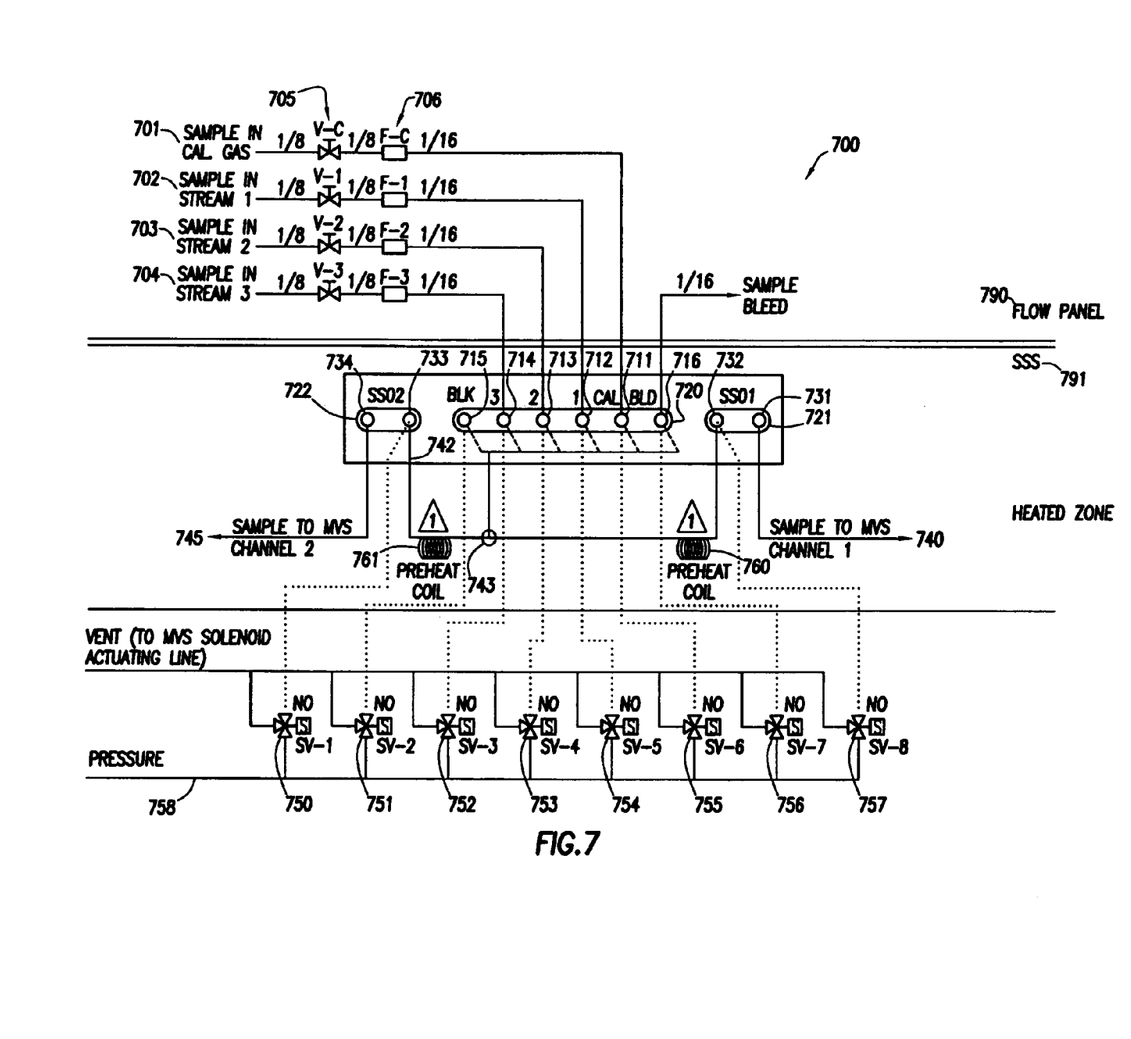
FIG. 7 is an improved stream switching system according to another embodiment of the invention.
Figure 8:
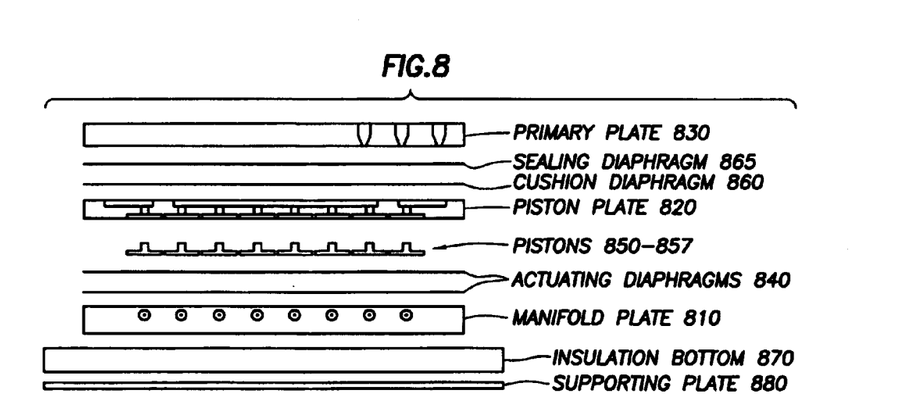
FIG. 8 is a preferred embodiment of the stream switching system of FIG. 7.

Other improvements to the system include the manner of maintaining a target temperature for a stream switching system. Often in previous systems, the stream switching portion of the system was not heated. Even where this portion was heated, it was difficult to maintain a constant temperature because of the large mass and size of the stream switching portion. In contrast, FIGS. 7–8 illustrate improvements to the stream switching system of FIGS. 3 and 4.

FIGS. 7–15B illustrate stream switching portions designed to maintain an elevated temperature within a narrow range. Stream switching system 700 includes a flow panel portion 790 upstream of sample wetted portion 791. Flow panel portion includes inputs for calibration 701, stream 1 702, stream 2 703, and stream 3 704. Streams 701–704 include respective valves 705 and respective particulate filters 706 along each stream's length prior to entry of the sample wetted portion of the stream switching system.

Streams 701–704 supply various fluid samples to the sample wetted portion, and connect respectively to actuatable calibration port 711 and actuatable stream ports 712–714. Actuatable ports 715–716 and 732–733, as well as ports 731 and 734, are also part of the sample wetted portion 791. Each actuatable port may be actuated into either an open or closed state as controlled by eight connected solenoids 750–757 (SV1–SV8) which correspond respectively to ports 711–716, 732–733. When a port is in an open state, fluid may pass freely through the port. When a port is in a closed state, fluid is prevented from flowing through that port. Also shown in FIG. 7 are solenoid pressure line 758 and solenoid vent line 759.

As is explained farther below, each actuatable stream port 712–714, as well as actuatable calibration port 711, is positioned in an area 720 that creates a common sample path. Also positioned in the common sample path 720 are an actuatable "blocking" port 715 and an actuatable "bleed" port 716. In addition, area 721 creates a first sample shut off that contains tube "blocking" ports 732 and 731. Area 722 creates a second sample shut off that contains two "blocking" ports 733, and port 734. As shown, ports 732 and 733 are actuatable, while ports 731 and 734 are not. It is to be understood that all of these ports could be actuatable, or ports 731 and 734 could be actuatable while ports 732 and 733 are not.

Two channels, channel 1 740 and channel 2 745, are output tubing that direct fluid sample away from the stream switching portion. A first flow restrictor and pre-heat coil 760 is in association with coil 1, and a second flow restrictor and preheat coil 761 is in association with coil 2. More specifically, first pre-heat coil 760 is located between "T" point 743 and the first sample shut off. Second pre-heat coil 761 is located between "T" point 743 and the second sample shut off.

This stream switching system operates in generally the same manner as the stream switching system of FIG. 3. However, as sample flows through the respective flow restrictors and pre-heat coils 760, 761, the sample is heated. This heating of the sample, if desired, accomplishes two goals. First, the sample must preferably be introduced to the gas chromatograph as a single phase sample instead of a two-phase liquid/gas sample. Temperatures above about 80 degrees Fahrenheit are normally adequate to maintain a gaseous sample of most hydrocarbon process streams at a sample pressure of 15–25 psi. Second, an elevated temperature (preferably near the chromatograph temperature) for the sample is desirable for the optimal operation of the gas chromatograph. Thus, the "pre-heating" of the sample helps to achieve a more accurate measurement of the sample's composition by the gas chromatograph. Further, the pre-heat coil additionally acts as a restriction column to flow because of a small inner diameter. By selecting the proper diameter tubing, the sample flow at the vent is reduced from an unobstructed 200–250 cc/minute at 15 psig inlet pressure to about 50–70 cc/min at 15 psig. The increased control over sample flow rate given by the pre-heat coil allows simultaneous analysis by gas chromatographs downstream to each coil.

An accompanying inventive feature is an insulative design that stabilizes temperature variations in the stream switching system. The preferred insulative design changes depend on whether the application is Division 1 or Division 2. A Division 1 application is in an area where the hazard can exist under normal operating conditions. A Division 2 application is in area where ignitable gases or vapors are handled, processed, or used, but which are normally closed containers or closed systems from which they can only escape through accidental rupture or breakdown of such containers or systems.

FIG. 8 illustrates a stream switching system appropriate for Division 1 application. A lower plate, referred to as a manifold plate 810, includes eight actuation ports. The middle plate, also called a piston plate 820, includes eight locations designed to receive respective pistons 850–857. Middle plate 820 also includes grooves, shallow channels or chambers that form areas 720–722, as described with reference to FIG. 7. The upper plate, referred to as the primary plate 830, includes screw holes corresponding to torque screws, as well as fluid ports. Eight pistons 850–857 (corresponding to ports 711–716, 732–733) as well as a pair of actuating diaphragms 840 lie between manifold plate 810 and middle plate 820. These diaphragms ensure a leak-free fit between each pair of plates and between a piston and its corresponding port. The actuating diaphragm may be made from Kapton of about 3 mm thickness. Sealing diaphragm 865 and cushion diaphragm 860 lie between the primary plate 830 and middle plate 820. The sealing diaphragms may be made from Teflon-coated Kapton. Supporting plate 880 attaches to and supports insulation plate 870, which in turn attaches to the bottom of manifold plate 810.

Figure 9:
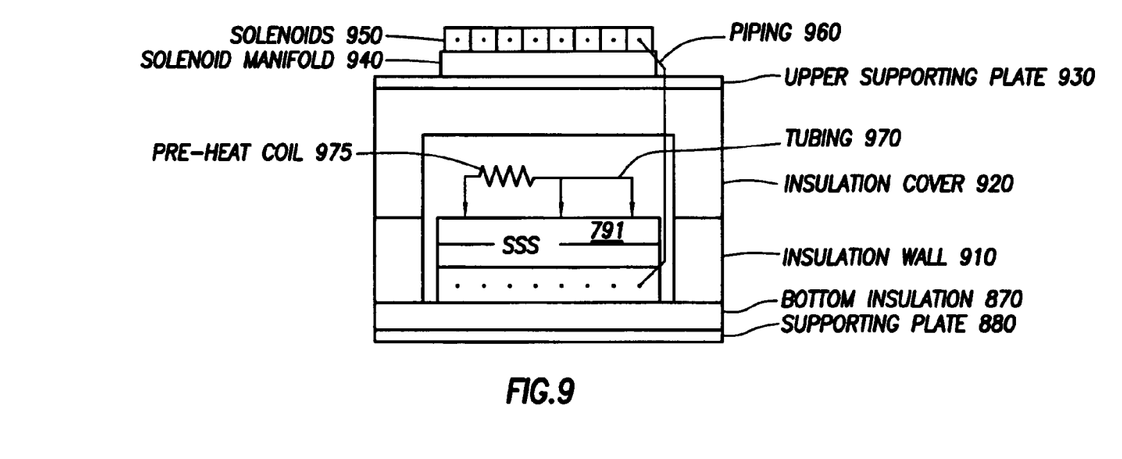
FIG. 9 is a preferred Division 1 implementation of the stream switching system of FIG. 8.

FIG. 9 includes the stream switching system 791 of FIGS. 7 and 8 in an insulative housing. In order to stabilize the temperatures in heated zones, an "oven" is created from a thermal insulation material. This oven is essentially a sleeve that surrounds the rest of the stream switching system and keeps its temperature stable, except for the solenoids, which must be kept away from the heat inside the oven. Insulation wall 910 surrounds stream switching system 791 and connects to both bottom insulation 870 and to insulation cover 920. Attached to and supporting insulation cover 920 is upper supporting plate 930. Supporting plate 930 also attaches to solenoid manifold 940 which, in turn, connects to eight solenoids 950. Piping 960 connects solenoids 950 to manifold plate 810. To simplify the illustration, only a single piping tube 960 is shown, but it is to be understood that in the preferred embodiment each solenoid 950 connects via a separate piping to the manifold plate 810. Also illustrated are tubing 970 attached to the stream switching system 791, and one or more pre-heat coils 975, as explained with reference to FIG. 7. One or more heaters such as silicon rubber heaters may be located on the side of the stream switching system assembly to warm and stabilize the temperature of stream switching system 791. Insulative housing is preferably made from foam material, manufactured by and available from Rogers InC. The entire assembly may be aligned by dowel pins and attached together by a plurality of screws that protrude through the insulative housing. The assembly may then be located in an explosion-resistant container suitable for the Division 1 environment.

Figure 10A:
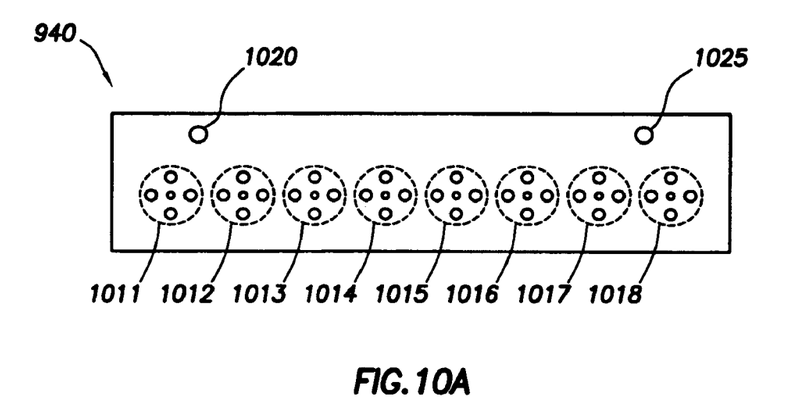
FIG. 10A is a top view of a Division 1 solenoid manifold.
Figure 10B:
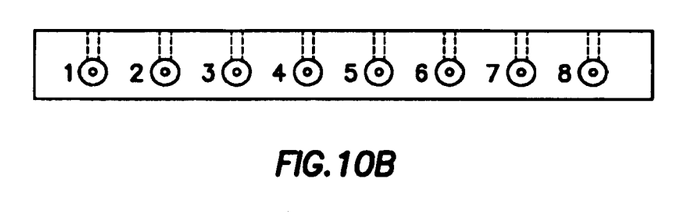
FIG. 10B is a side view of a Division 1 solenoid manifold.

FIGS. 10A and 10B show a Division 1 solenoid manifold 940. Solenoid manifold 940 includes eight regions 1011–1018 corresponding to eight solenoids. Each region 1011–1018 contains five holes corresponding to an input pressure line, a release line, an actuation gas line, and two mounting holes. As shown in FIG. 10B, the Division 1 solenoid manifold includes eight side portals corresponding to the piping that connects the solenoid manifold 940 and the manifold plate 810. Hoes 1020, 1025 are screw holes.

Figure 11A:
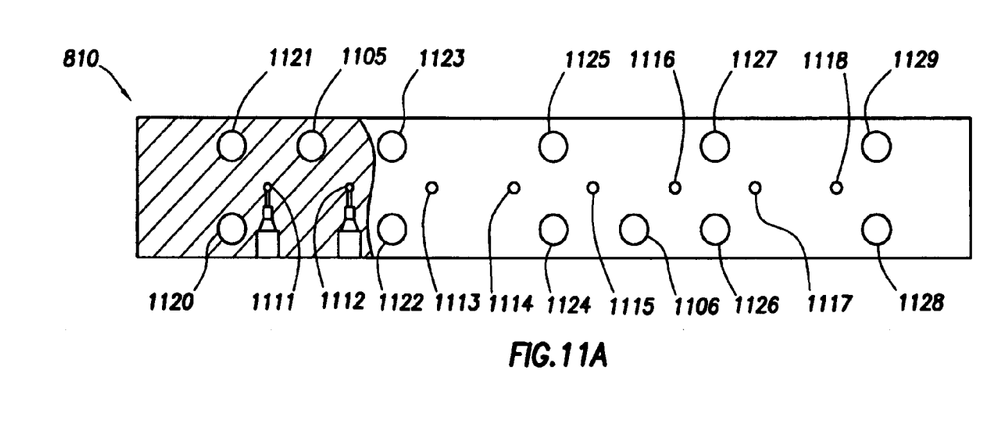
FIG. 11A is a top view of a Division 1 manifold.
Figure 11B:
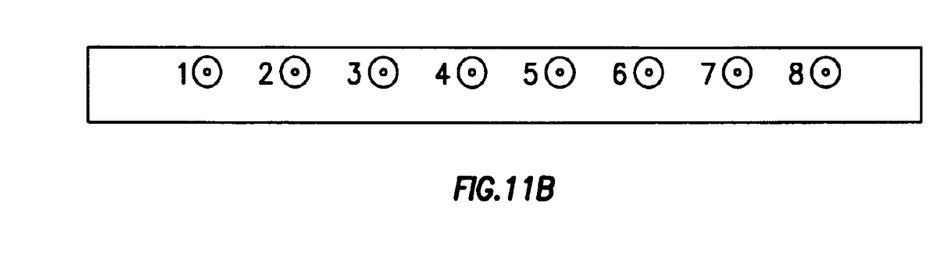
FIG. 11B is a side view of a Division 1 manifold.

FIGS. 11A and 11B show a Division 1 manifold plate 810. Manifold plate 810 includes ten screw holes 1110–1119 suitable for torque screws, and two dowel pin holes 1105, 1106. Gas pressure from the solenoids travels through eight portals 1111–1118 to actuate the pistons.

Figure 12:
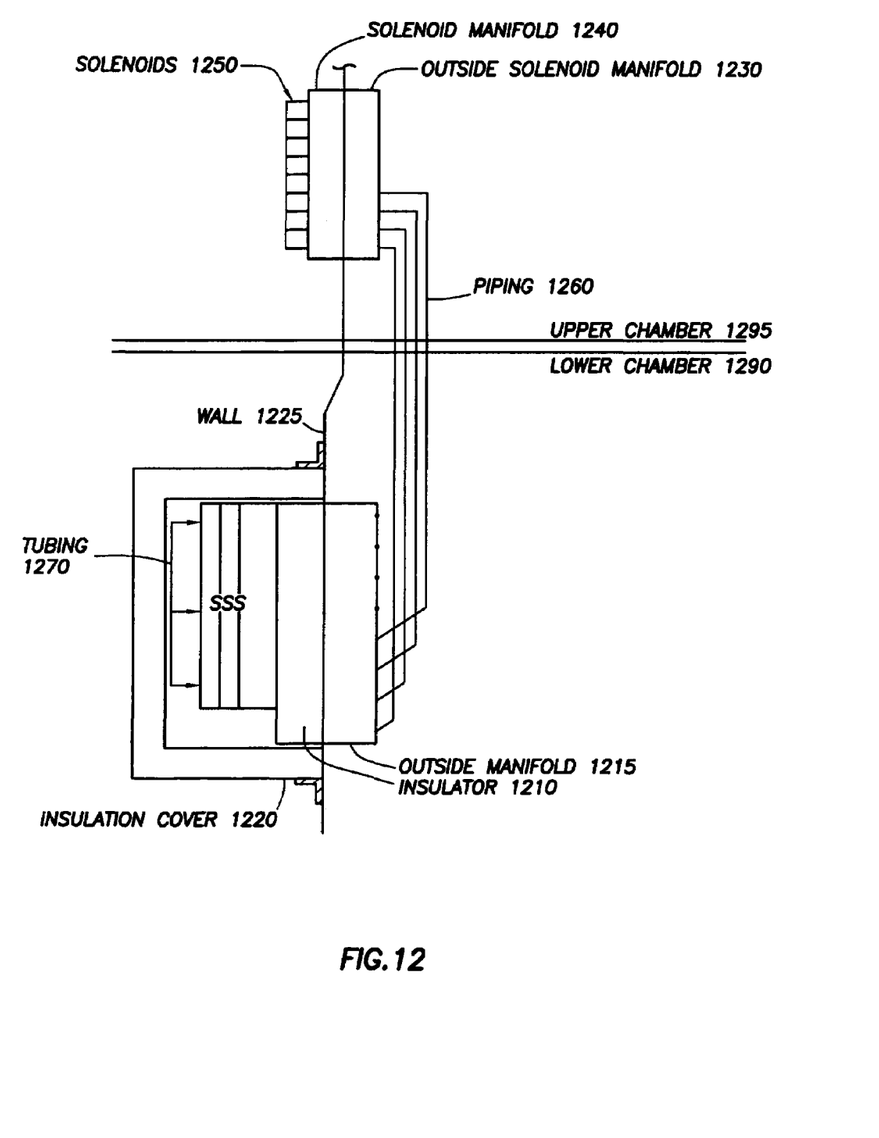
FIG. 12 is a preferred Division 2 implementation of the stream handling system of FIG. 8.

FIG. 12 illustrates a system containing a stream switching system appropriate for Division 2 application. This Division 2 system is typically wall mounted, and is divided into a lower (sample) enclosure 1290 and an upper (electronics) enclosure 1295. Lower enclosure 1290 includes a stream switching system 791 proximate to an opening in wall 1225. Stream switching system 791 attaches at its bottom to an insulator 1210. Insulator 1210, preferably made from Teflon, connects to an outside manifold 1215. On its bottom, outside manifold 1215 contains eight pressure input locations corresponding to the eight pistons of the stream switching system. The stream switching system is encased in an insulation cover 1220 that is anchored to wall 1225. Also inside insulation cover 1220 may be tubing 1270 or one or more heating coils. Upper enclosure 1295 includes a set of solenoids 1250 attached to a solenoid manifold 1240 and outside solenoid manifold 1230. Piping 1260 connects outside solenoid manifold 1230 to outside manifold 1215. The Teflon insulator 1210 is a trademark of DuPont.

Figure 13:
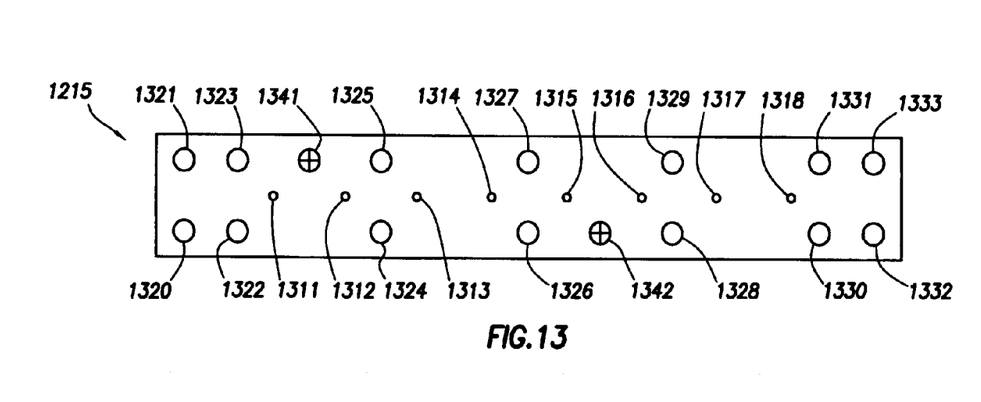
FIG. 13 is a top view of a Division 2 manifold.

FIG. 13 shows a Division 2 outside manifold 1215. Eight ports correspond to the eight pistons of the preferred embodiment. Fourteen torque screw holes 1320–1333 for torque screws are also shown, in addition to two dowel pin holes 1341, 1342 suitable for dowel pins.

Figure 14:
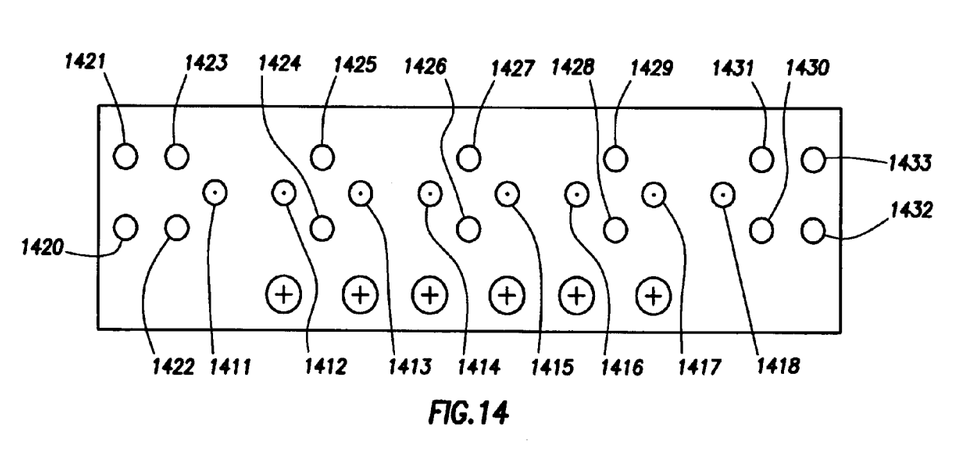
FIG. 14 is a top view of a Division 2 bottom insulator.
Figure 15A:
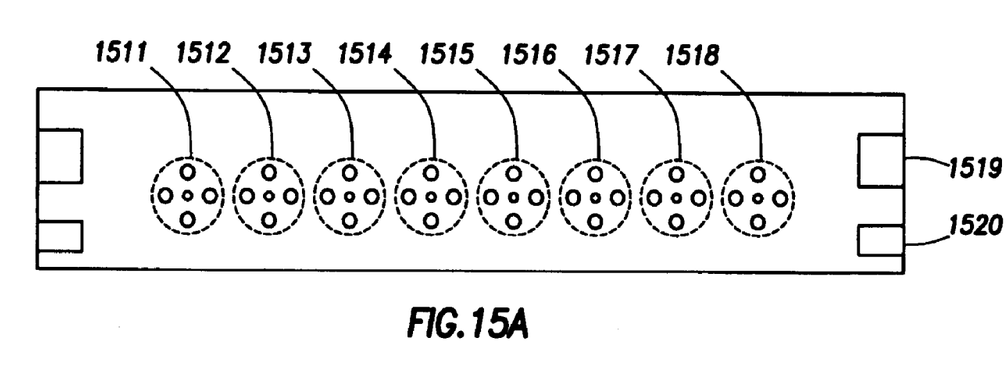
FIG. 15A is a top view of a Division 2 solenoid manifold.
Figure 15B:
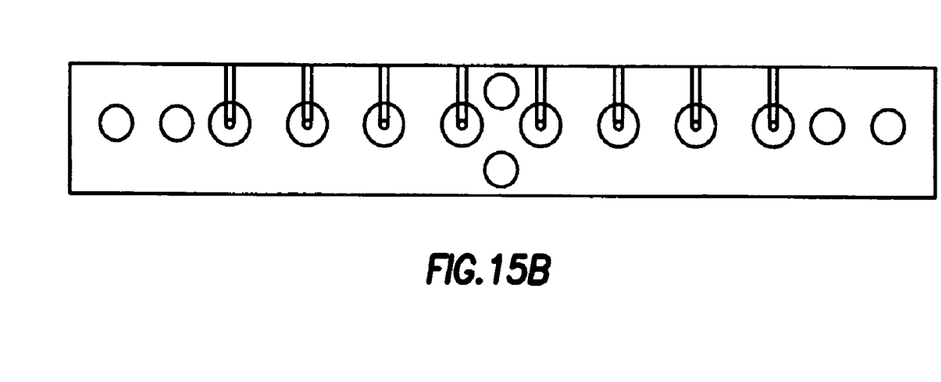
FIG. 15B is a side view of a Division 2 solenoid manifold.

FIG. 14 shows a bottom insulator 1210 that connects to outside manifold 1215. Bottom insulator 1210 includes eight through holes 1411–1418 for communicating gas pressure to the pistons of the stream switching system. Fourteen torque screw holes 1420–1433 receive the same torque screws as placed through the outside manifold 1215. Six through holes for tubing fitting connection FIGS. 15A and 15B show an upper or outer solenoid manifold 1230. Included are eight regions 1511–1518 corresponding to eight solenoids. Each region 1511–1518 contains five holes corresponding to an input pressure line, a release line, an actuation gas line, and two mounting holes. Also shown are actuating gas supply line 1519 and vent line 1520.

Referring back to FIG. 7, another improvement is the use of solenoids 750–757 to increase safety. If conventional electronically-actuated solenoids are utilized with the stream switching system of FIG. 7, upon a power failure gas sample will flow freely through the sample handling system, resulting in a risk of explosion and waste of gas. In the preferred embodiment, the solinoids are also switched electronically. Under normal operating conditions, however, the solenoid used with the invention is "open." When these solenoids 750–757 are open, actuating gas can flow into the valve to push the pistons into an upper, elevated position, stopping sample flow. Thus, upon a power failure or similar mishap, the solenoids 750–757 are open and the stream switching system of FIG. 7 will stop the sample flow. This significantly lessens the chance of explosion. These solenoids "close" only upon the application of actuation gas from the pressure line, which requires electrical power.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims that follow, the scope of which shall include all equivalents of the subject matter of the claims.

What is claimed is:

1. A stream switching system, comprising:
 a stream switching housing having at least one common stream channel portion with a plurality of input ports and at least one output port;
 tubing connected at least one of said output ports,
 said tubing at least in part being a pre-heat coil suitable to heat a fluid sample traveling through said coil and to act as a flow restrictor for flow restriction of said fluid sample, the extent of said flow restriction sufficient to restrict said sample flow to about 50–70 cc/mm.

2. The stream switching system of claim 1, further comprising:
 an insulated housing forming an interior region and encapsulating said stream switching housing in said interior region, said insulated housing stabilizing a temperature of said stream switching housing.

3. The stream switching system of claim 2, further comprising a heater within said interior region.

4. The stream switching system of claim 3, wherein said fluid flow actuation switches connect to said insulated housing.

5. The stream switching system of claim 3, wherein said fluid flow actuation switches are remote from said insulated housing.

6. The stream switching system of claim 2, further comprising:
 a plurality of gas flow actuation switches positioned outside of said insulated housing;
 piping connecting said plurality of fluid flow actuation switches to said insulated housing.

7. The stream switching system of claim 6, wherein said fluid flow actuation switches are solenoids.

8. The stream switching system of claim 7, wherein said piping connects said solenoid to said stream switching housing.

9. The stream switching system of claim 1, wherein there are more input ports than output ports.

10. The stream switching system of claim 1, further comprising at least one sample shut off switch connected to a downstream end of said tubing.

11. The stream switching system of claim 10, wherein said sample shut off switch includes a bleed port.

12. The stream switching system of claim 1, wherein each of input ports and output ports are individually actuatable.

13. A stream switching system, comprising:
 a housing forming an interior flow path for gas samples, said flow path connecting to the exterior of said housing via a first number of input ports and a second number of output ports, wherein said number of input ports is greater than said number of output ports; and
 piping connected to at least one of said output ports, said piping heating said gas samples to about a predetermined temperature.

14. The stream switching system of claim 13, wherein said housing further forms a sample shut off channel with an external bleed port, and further wherein said piping is upstream of said sample shut off channel.

15. A stream switching system, comprising:
 a stream switching housing having at least one common stream channel portion with a plurality of input ports and at least one output port;
 tubing connected at least one of said output ports;
 insulation surrounding said stream switching housing and said tubing;
 a heater to warm said stream switching housing and said tubing to a predetermined temperature;
 said tubing at least in part being a pre-heat coil suitable to heat a fluid sample having a liquid portion and to act as a flow restrictor for flow restriction of said fluid sample such that said fluid sample is heated to said predetermined temperature.

16. The stream switching system of claim 15, wherein said predetermined temperature is eighty degrees Fahrenheit.

17. The stream switching system of claim 15, further comprising:
 a gas chromatograph attached to said output port;
 wherein said gas chromatograph is maintained at a second predetermined temperature and said predetermined temperature for said fluid sample is the same as said second predetermined temperature.

* * * * *